(12) United States Patent
Svendsen

(10) Patent No.: US 7,721,738 B2
(45) Date of Patent: May 25, 2010

(54) COUPLING ARRANGEMENT

(75) Inventor: Gunnar N. Svendsen, Jyllinge (DK)

(73) Assignee: Unomedical A/S, Lynge (DK)

( * ) Notice: Subject to any disclaimer, the term of this patent is extended or adjusted under 35 U.S.C. 154(b) by 381 days.

(21) Appl. No.: 10/240,885

(22) PCT Filed: Apr. 5, 2001

(86) PCT No.: PCT/DK01/00231

§ 371 (c)(1),
(2), (4) Date: Oct. 4, 2002

(87) PCT Pub. No.: WO01/76672

PCT Pub. Date: Oct. 18, 2001

(65) Prior Publication Data

US 2003/0056787 A1 Mar. 27, 2003

(30) Foreign Application Priority Data

Apr. 6, 2000 (DK) ................. 2000 00580

(51) Int. Cl.
*A61M 16/00* (2006.01)
(52) U.S. Cl. ............... 128/207.14; 128/202.27; 128/912
(58) Field of Classification Search ........... 128/202.27, 128/207.14, 207.17, 207.18, 207.15, 207.16, 128/910, 911, 912; 29/506; 285/322, 324, 285/256, 257, 247, 250, 251, 245, 386
See application file for complete search history.

(56) References Cited

U.S. PATENT DOCUMENTS

| 2,434,975 A | * | 1/1948 | Woodling ............. 285/334.5 |
| 2,694,584 A | * | 11/1954 | Miller ................. 285/250 |
| 3,469,582 A | | 9/1969 | Jackson |
| 3,517,669 A | | 6/1970 | Buono et al. |
| 3,595,445 A | | 7/1971 | Buford et al. |
| 3,902,500 A | | 9/1975 | Dryden |
| 3,957,295 A | * | 5/1976 | Gould et al. ............. 285/342 |
| 3,958,566 A | | 5/1976 | Furihata |
| 3,991,762 A | | 11/1976 | Radford |
| 4,105,226 A | * | 8/1978 | Frey et al. ............. 285/148.21 |

(Continued)

FOREIGN PATENT DOCUMENTS

EP 0 204 311 A2 3/1986

(Continued)

OTHER PUBLICATIONS

European Search Report, dated Apr. 16, 2004.

(Continued)

*Primary Examiner*—Darwin P Erezo
(74) *Attorney, Agent, or Firm*—Finnegan, Henderson, Farabow, Garrett & Dunner, L.L.P.

(57) ABSTRACT

A coupling arrangement for a system for endotracheal ventilation of a patient is disclosed. The system includes an endotracheal tube and a manifold configured for allowing ventilation of the patient via the endotracheal tube, which manifold has a first coupling element with an axial extent and with engagement element; and which endotracheal tube has a second coupling element with an axial extent and with engagement element; wherein the coupling arrangement is configured to produce, when the first and the second coupling elements are moved together in the axial direction, a locking engagement between the engagement elements.

8 Claims, 3 Drawing Sheets

U.S. PATENT DOCUMENTS

| | | | |
|---|---|---|---|
| 4,180,066 A | 12/1979 | Milliken et al. | |
| 4,266,815 A | 5/1981 | Cross | |
| 4,287,889 A | 9/1981 | Stupar | |
| 4,452,473 A | 6/1984 | Ruschke | |
| 4,510,933 A | 4/1985 | Wendt et al. | |
| 4,534,542 A | 8/1985 | Russo | |
| 4,537,182 A | 8/1985 | Otani | |
| 4,561,428 A | 12/1985 | Konomura | |
| 4,610,664 A | 9/1986 | Harle | |
| 4,638,539 A | 1/1987 | Palmer | |
| 4,673,393 A | 6/1987 | Suzuki et al. | |
| 4,696,296 A | 9/1987 | Palmer | |
| 4,722,366 A | 2/1988 | Maaskamp | |
| 4,735,441 A | 4/1988 | Stephens | |
| 4,825,859 A | 5/1989 | Lambert | |
| 4,834,726 A | 5/1989 | Lambert | |
| 4,836,199 A | 6/1989 | Palmer | |
| 4,838,255 A | 6/1989 | Lambert | |
| 4,846,167 A | 7/1989 | Tibbals | |
| 4,850,350 A | 7/1989 | Jackson | |
| 4,867,153 A | 9/1989 | Lorenzen et al. | |
| 4,872,579 A | 10/1989 | Palmer | |
| 4,938,741 A | 7/1990 | Lambert | |
| 4,967,743 A | 11/1990 | Lambert | |
| 4,981,466 A | 1/1991 | Lumbert | |
| 5,009,391 A | 4/1991 | Steigerwald | |
| 5,025,806 A | 6/1991 | Palmer et al. | |
| 5,060,646 A | 10/1991 | Page | |
| 5,065,754 A | 11/1991 | Jensen | |
| 5,073,164 A | 12/1991 | Hollister et al. | |
| 5,083,561 A | 1/1992 | Russo | |
| 5,107,829 A | 4/1992 | Lambert | |
| 5,116,088 A * | 5/1992 | Bird | 285/319 |
| 5,120,305 A | 6/1992 | Boehringer et al. | |
| 5,125,893 A | 6/1992 | Dryden | |
| 5,133,345 A | 7/1992 | Lambert | |
| 5,134,996 A | 8/1992 | Bell | |
| 5,139,018 A | 8/1992 | Brodsky et al. | |
| 5,140,983 A | 8/1992 | Jinotti | |
| 5,158,569 A | 10/1992 | Strickland et al. | |
| 5,163,926 A | 11/1992 | Bailey et al. | |
| 5,176,415 A * | 1/1993 | Choksi | 285/331 |
| 5,181,908 A | 1/1993 | Bell | |
| 5,184,611 A | 2/1993 | Turnbull | |
| 5,215,522 A | 6/1993 | Page et al. | |
| 5,220,916 A | 6/1993 | Russo | |
| 5,254,098 A | 10/1993 | Ulrich et al. | |
| 5,255,676 A | 10/1993 | Russo | |
| 5,269,756 A | 12/1993 | Dryden | |
| 5,269,768 A | 12/1993 | Cheung | |
| 5,277,177 A | 1/1994 | Page et al. | |
| 5,279,549 A | 1/1994 | Ranford | |
| 5,300,043 A | 4/1994 | Devlin et al. | |
| 5,309,902 A | 5/1994 | Kee et al. | |
| 5,325,850 A | 7/1994 | Ulrich et al. | |
| 5,325,851 A | 7/1994 | Reynolds et al. | |
| 5,333,606 A | 8/1994 | Schneider et al. | |
| 5,333,607 A | 8/1994 | Kee et al. | |
| 5,335,655 A | 8/1994 | Kee | |
| 5,337,780 A | 8/1994 | Kee | |
| 5,349,950 A | 9/1994 | Ulrich et al. | |
| 5,355,876 A | 10/1994 | Brodsky et al. | |
| 5,368,017 A | 11/1994 | Sorenson et al. | |
| 5,377,672 A | 1/1995 | Kee | |
| 5,419,769 A | 5/1995 | Devlin et al. | |
| 5,433,195 A | 7/1995 | Kee et al. | |
| 5,445,141 A | 8/1995 | Kee et al. | |
| 5,449,348 A | 9/1995 | Dryden | |
| 5,456,675 A | 10/1995 | Wolbring et al. | |
| 5,460,613 A | 10/1995 | Ulrich et al. | |
| 5,487,381 A | 1/1996 | Jinotti | |
| 5,490,503 A * | 2/1996 | Hollister | 128/205.12 |
| 5,496,287 A | 3/1996 | Jinotti | |
| 5,513,628 A | 5/1996 | Coles et al. | |
| 5,562,618 A | 10/1996 | Cai et al. | |
| 5,579,762 A * | 12/1996 | Lee | 128/207.14 |
| 5,582,161 A * | 12/1996 | Kee | 128/200.26 |
| 5,582,166 A * | 12/1996 | Lee | 128/207.14 |
| 5,598,840 A | 2/1997 | Iund et al. | |
| 5,611,336 A | 3/1997 | Page et al. | |
| 5,613,663 A | 3/1997 | Schmidt et al. | |
| 5,628,306 A | 5/1997 | Kee | |
| 5,632,729 A | 5/1997 | Cai et al. | |
| 5,636,625 A | 6/1997 | Miyagi et al. | |
| 5,642,726 A | 7/1997 | Owens et al. | |
| 5,645,048 A | 7/1997 | Brodsky et al. | |
| 5,664,564 A | 9/1997 | Palmer | |
| 5,664,594 A | 9/1997 | Kee | |
| 5,669,380 A | 9/1997 | Garry et al. | |
| 5,676,136 A | 10/1997 | Russo | |
| 5,694,922 A | 12/1997 | Palmer | |
| 5,702,374 A * | 12/1997 | Johnson | 604/533 |
| 5,730,123 A | 3/1998 | Lorenzen et al. | |
| 5,735,271 A | 4/1998 | Lorenzen et al. | |
| 5,738,091 A | 4/1998 | Kee et al. | |
| 5,775,325 A | 7/1998 | Russo | |
| 5,779,687 A | 7/1998 | Bell et al. | |
| 5,791,337 A | 8/1998 | Coles et al. | |
| 5,794,986 A * | 8/1998 | Gansel et al. | 285/148.16 |
| 5,827,218 A | 10/1998 | Nguyen et al. | |
| 5,830,214 A | 11/1998 | Flom et al. | |
| 5,855,562 A | 1/1999 | Moore et al. | |
| 5,864,938 A * | 2/1999 | Gansel et al. | 29/506 |
| 5,919,174 A | 7/1999 | Hanson | |
| 5,993,437 A * | 11/1999 | Raoz | 604/536 |
| 6,012,451 A | 1/2000 | Palmer | |
| 6,070,582 A | 6/2000 | Kee | |
| 6,135,110 A | 10/2000 | Roy | |
| 6,148,857 A | 11/2000 | West et al. | |
| 6,190,372 B1 | 2/2001 | Racz | |
| 6,227,200 B1 | 5/2001 | Crump et al. | |
| 6,254,061 B1 | 7/2001 | Levine et al. | |
| 6,254,589 B1 | 7/2001 | Raoz | |
| 6,415,789 B1 | 7/2002 | Freitas et al. | |
| 6,494,203 B1 | 12/2002 | Palmer | |
| 6,543,451 B1 | 4/2003 | Crump et al. | |
| 6,575,944 B1 | 6/2003 | McNary et al. | |
| 6,588,425 B2 | 7/2003 | Rouns et al. | |
| 6,588,427 B1 | 7/2003 | Carlsen et al. | |
| 6,602,219 B2 | 8/2003 | Madsen et al. | |
| 6,609,520 B1 | 8/2003 | Carlsen et al. | |
| 2001/0029953 A1 | 10/2001 | Mattar Neto et al. | |
| 2001/0044600 A1 | 11/2001 | Elkins | |
| 2003/0047704 A1 | 3/2003 | Svendsen | |
| 2003/0056787 A1 | 3/2003 | Svendsen | |
| 2003/0106558 A1 | 6/2003 | Cardon | |
| 2003/0106559 A1 | 6/2003 | Svendsen | |

FOREIGN PATENT DOCUMENTS

| | | |
|---|---|---|
| EP | 0 360 471 A2 | 9/1989 |
| EP | 0349745 A1 | 1/1990 |
| EP | 0 633 038 A1 | 1/1995 |
| EP | 0733380 A1 | 9/1996 |
| EP | 0633038 B1 | 7/1998 |
| EP | 1208865 A2 | 5/2002 |
| EP | 1210957 A1 | 6/2002 |
| GB | 2023249 A | 12/1979 |
| GB | 2123106 A | 1/1984 |
| GB | 2270845 A | 3/1994 |
| WO | WO 93/17742 A1 | 9/1993 |
| WO | WO 93/21981 A2 | 11/1993 |
| WO | WO 95/31240 A1 | 11/1995 |
| WO | WO 95/31250 A1 | 11/1995 |

| | | |
|---|---|---|
| WO | WO 96/09082 A1 | 3/1996 |
| WO | WO 96/26757 A1 | 9/1996 |
| WO | WO 96/30069 A1 | 10/1996 |
| WO | WO 98/10808 A2 | 3/1998 |
| WO | WO 98/33536 | 8/1998 |

OTHER PUBLICATIONS

Photographs (Figs. 1-5) and photocopy of product label of Steri Cath® DL Closed Ventilation Suction System, Cat. No. 6110-14.

* cited by examiner

COUPLING ARRANGEMENT

The present invention relates to a coupling arrangement of the kind described in the preamble to claims 1 and 2. The coupling arrangement can be used for connecting a manifold of the kind described in eg WO98/33536 and U.S. Pat. No. 5,487,381 to an endotracheal tube.

BACKGROUND OF THE INVENTION

It is commonly known to configure the end of an endotracheal tube with a conically tapering male coupling means that is introduced into a complementarily configured female coupling means on the manifold for establishing a sealing frictional connection. In order to separate the parts from each other it is necessary to produce an axial separation force. This force is typically produced by means of a disengagement means in the form of a wedge-shaped manifold or fork that is wedged between two protruding flanges located at the end of the female and the male coupling means, respectively.

However, it has been found that by use of said manifold in practice, it is difficult for the hospital staff to avoid laterally oriented power influences on the coupling means and thus on the endotracheal tube that has been inserted into the patient with ensuing traumatic consequences for the patient. Besides, the prior art solutions involve a risk that the manifold disappears. In given situations, the latter has entailed that the hospital staff have attempted to separate the coupling means manually, which has, to an even wider extent, traumatically influenced the patient due to laterally oriented power influences.

BRIEF SUMMARY OF THE INVENTION

It is the object of the invention to solve the above-mentioned problems by the prior art. As featured in the characterising portions of claims 1 and 2 this is obtained by arranging a thread for a disengagement means on either the manifold or in connection with the endotracheal tube. By the solution thus provided it is ensured that, at any time, the separation force is oriented essentially in the axial direction, and that no power influences occur transversally to the coupling means. Additionally, it becomes possible to avoid that the disengagement means is lost.

It is also preferred that the coupling means are configured as male and female parts, respectively, as featured in claims 3 and 4. Preferably the coupling means are configured with engagement means in the form of complementary conical faces whereby it is possible to provide a frictional coupling in conventional manner as such. However, nothing prevents the engagement means from being configured in another manner, eg so as to provide a releasable joining by clipping together the engagement parts while profiting from the resilience of the constituent materials.

BRIEF DESCRIPTION OF THE SEVERAL VIEWS OF THE DRAWINGS

The invention will now be described in further detail with reference to the embodiments shown in the drawing. In the drawing.

DETAILED DESCRIPTION OF THE INVENTION

Figure 1:
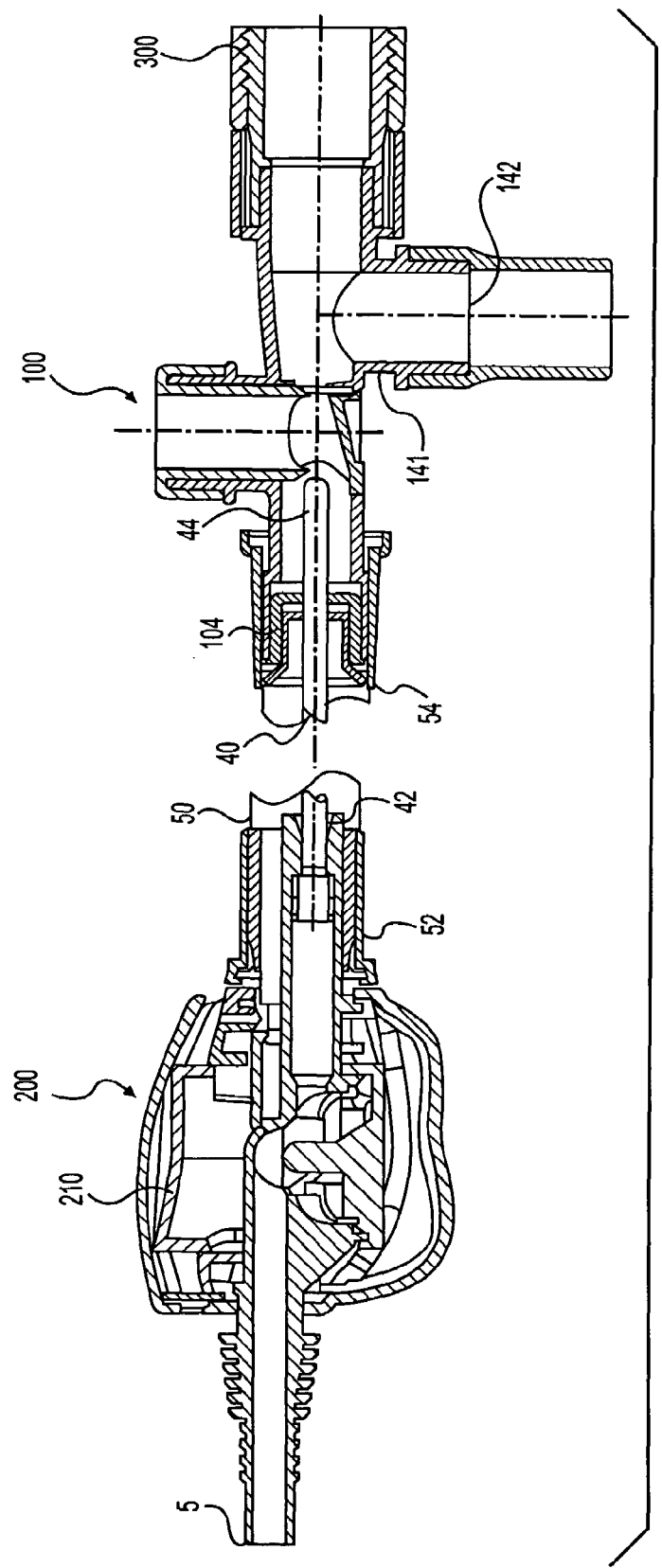
FIG. 1 illustrates a part of a system for endotracheal ventilation of a patient.

In principle, the functionality of the system shown in FIG. 1 corresponds to the functionality of eg the system described in DK patent application No 32/95. The system shown is thus suitable for performing ventilation as well as aspiration of a patient and is thus conventionally designated a 'closed' system. A flexible shrouding or pipe coupling 50 is thus, at its first end 52, connected to the valve device 200 and it is, at its opposite end 54, connected to a manifold 100. The valve housing 200 is configured for being, via a coupling 5, connected to a not shown suction device for generating a subatmospheric pressure in the system.

The manifold 100, which is preferably transparent, is also configured to be connected—via a coupling arrangement—to a tubular element or "tube" for endotracheal ventilation of a patient, ie a tube configured for being introduced into the respiratory tracts of the patient with a view to maintaining artificial ventilation of the patient. To this end, the manifold 100 has a coupling device, designated in the drawing by the reference numeral 300 and to be described in further detail below. An opening 142 in a ventilation stub 141 allows ventilation of the patient by means of a not shown conventional apparatus. To this end the ventilation stub 141 is preferably configured with a screw thread for connection with the ventilation apparatus.

Besides, the system conventionally comprises a catheter 40 that extends within the interior of the shrouding 50 and that can be introduced into the patient's respiratory tracts to draw out secretion. At its first end 42, the catheter 40 is securely connected to the valve device 200 and, at its opposite end 44, it is displaceably received in the manifold 100, the catheter being—via a packing 104—sealed relative to the shrouding 50 so as to prevent fluid from penetrating into the shrouding. Also, the packing 104 causes secretion to be scraped off the outside of the catheter 40 during withdrawal of the catheter from the patient. It will be understood that the opposite end 44 of the catheter forms a suction point that can, while the shrouding 50 is simultaneously folded, be displaced through the manifold interior and into the not shown tube for ventilation of the patient. By this movement, the end 44 of the catheter is thus conveyed to the right in FIG. 1. Hereby it is possible to perform regular suction of secretion from the patient's respiratory tracts, as the operator connects the system to the suction device by operating an actuator button 210 arranged in the valve housing 200.

As mentioned above, the manifold 100 has a coupling device that constitutes a first coupling means 300 of a coupling arrangement 300, 330, 400. This first coupling means is shown more clearly in FIG. 2, from where it will also appear that the manifold 100 defines a through-going axis A. In the embodiment shown the coupling means 300 is constituted by a separate pipe coupling that is configured for being able to be fastened in extension of the manifold 100 via an engagement area 150 on the outside of the manifold 100 and that extends along the axis A. However, the coupling means 300 may very well be formed integrally with the manifold 100. The coupling means 300 has an interiorly extending, through-going passage for ventilation and aspiration of the patient, and it has at its one end a first cylindrical area 310 that continues—via an annular plateau 312 that extends perpendicular to the axis A—into a cylindrical area 315 provided with an exterior thread 320.

Figure 3:
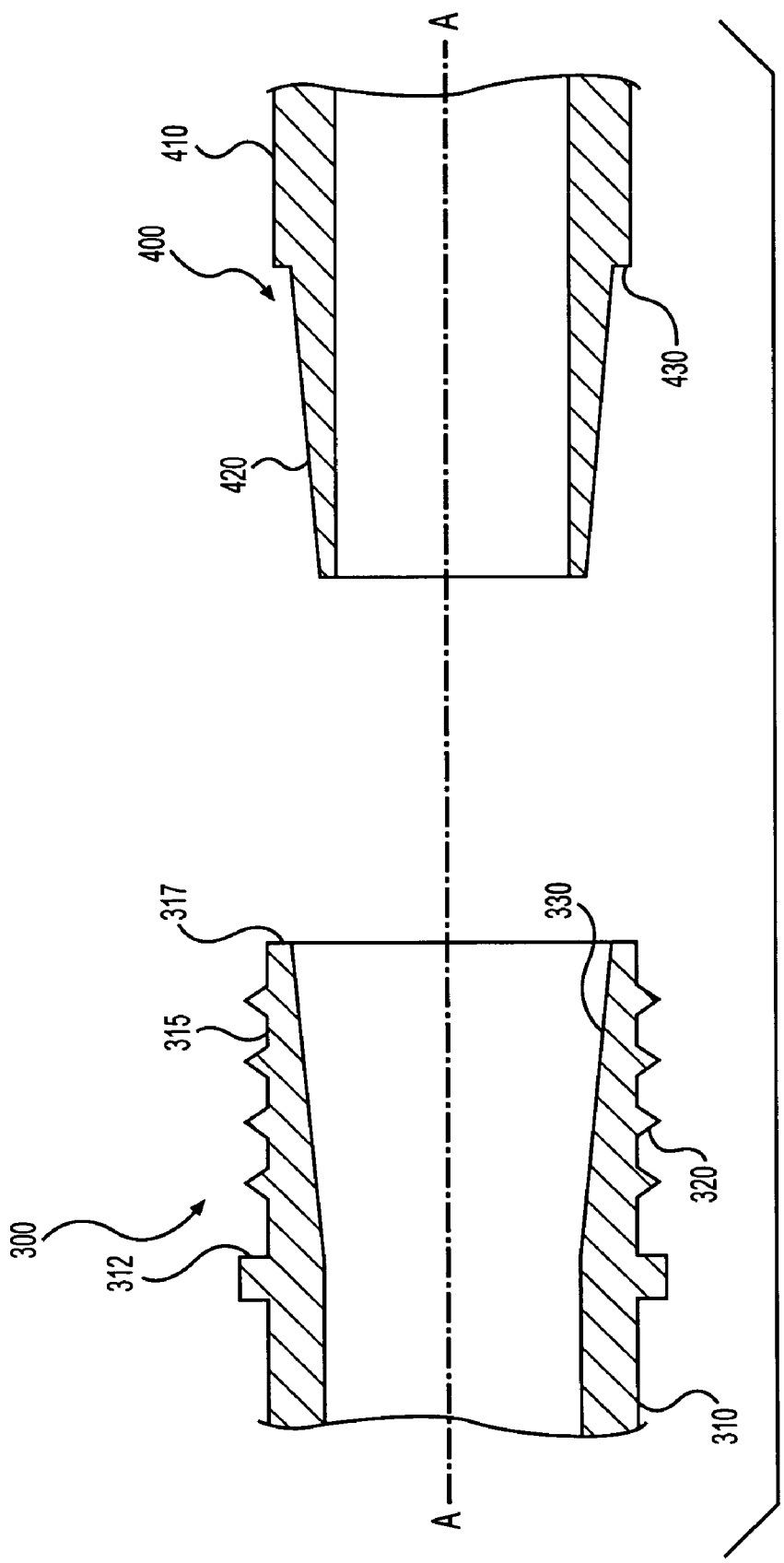
FIG. 3 is a cross sectional view through the coupling arrangement according to the invention, without the disengagement means.

In FIG. 3, the coupling arrangement is shown in further detail. To the left in the drawing the coupling means 300 thus shown that has, to the extreme right, an annular end edge 317. The passage in the cylindrical area 315 has, as will appear, an evenly increasing interior diameter in a direction away from the manifold 100, whereby it is possible to provide a frictional joint between the first coupling means 300 and a second coupling means 400, which is shown to the right in FIG. 3, and comprising an area 420 that is complementary with the area 315.

The second coupling means 400 is, as shown, configured as a cylindrical body with a through-going passage that extends along the axis A like the passage in the first coupling means 300. A tapering area 420 of the second coupling means 400 has an increasing, exterior diameter that has been adjusted in accordance with the change in the interior diameter of the passage within the area 315 in the first coupling means 300. Thereby it is possible to provide a sealing frictional coupling by introduction of the second coupling means 400 into the first coupling means 300. When the manifold 100 is to be connected to an endotracheal tube, said joining of the two coupling means is performed for establishing a very sealing frictional connection. The tapering of the passage within the area 315 and the area 420 can be comprised within the preferred ratio of about 1 to 40.

The second coupling means 400 also comprises a plateau 430 that extends perpendicular to the axis A, which plateau forms a transition between the tapering area 420 and a head portion 410 of the coupling means 400. The head portion 410 can either be solidly connected to the end of an endotracheal tube, or it can be configured for being solidly connected to the end of an endotracheal tube immediately preceding the introduction into the patient of the endotracheal tube. It will be understood that the first coupling means 300 will, in the relevant case, form a female coupling means, whereas the second coupling means 400 forms a male coupling means.

Figure 2:
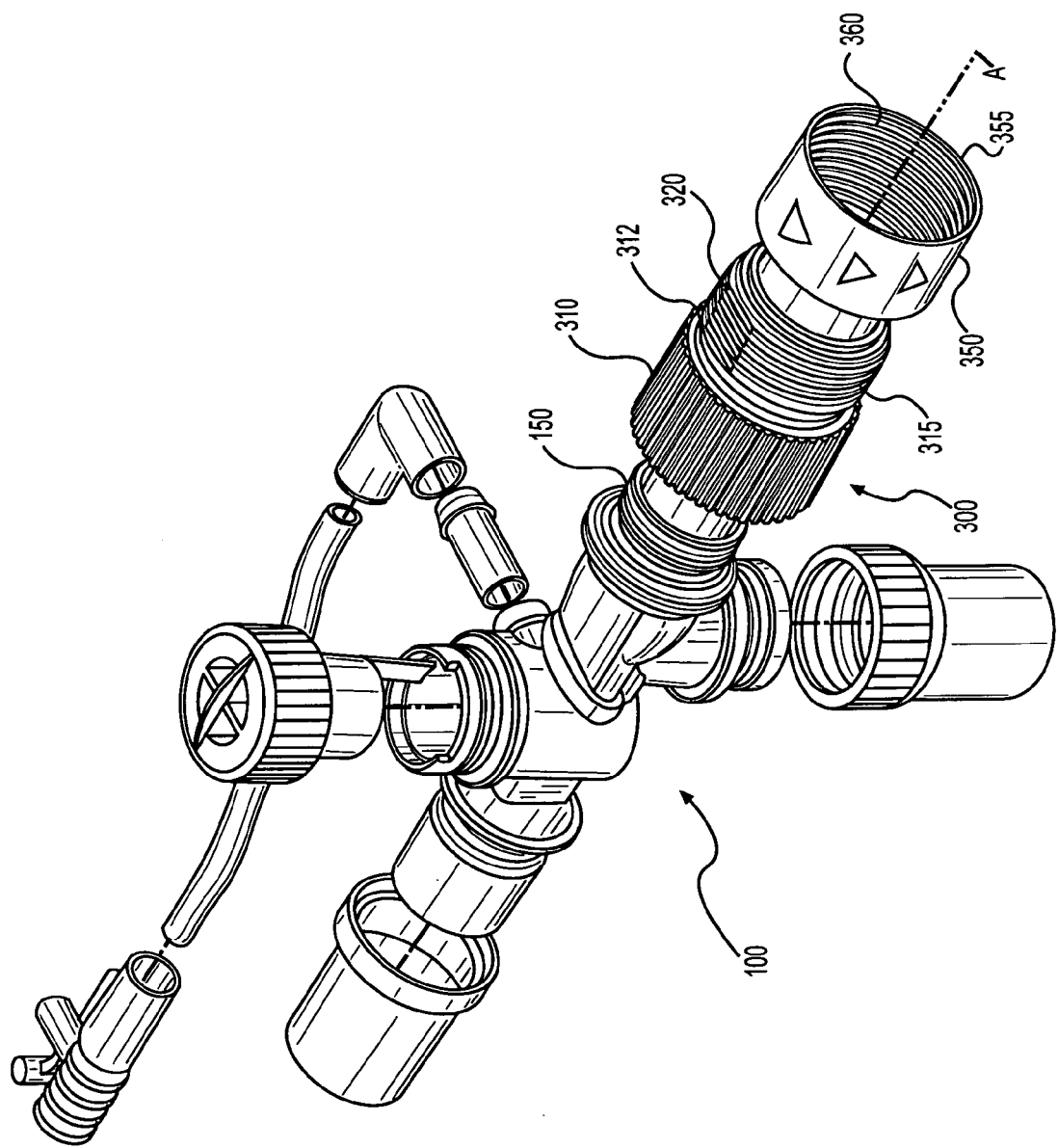
FIG. 2 illustrates a manifold in a perspective view and featuring a part of the coupling arrangement according to the invention.

Additionally the coupling arrangement comprises the disengagement means 350 shown in FIG. 2 that has an internal thread 360 configured for cooperating with the thread 320. The plateau 312 forms a first end position for the disengagement means 350, since preferably the extent of the disengagement means 350 along the axis A corresponds maximally to the extent of the thread 320 along the axis A.

When the second coupling means 400 has been introduced into the coupling means 300, the end edge 317 is preferably in abutment on the plateau 430. In this state, there will preferably be a certain distance between the plateau 430 and the disengagement means 350 that has been screwed onto the area 315. In order to be able, in this state, to perform a separation of the two coupling means, the disengagement means 350 is turned a suitable number of times, whereby the means 350 is displaced and caused to abut on the plateau 430. By carrying out a further manual turning of the disengagement means 350, an axial power influence is generated towards the second coupling means 400. The power influence is oriented in accordance with the axis A and will entail that the second coupling means 400 is released. The pitch of the threads 320, 360 can be selected in accordance with the forces involved, including the ease with which the user must be able to turn the disengagement means 350 in order to achieve the intended separation.

The invention claimed is:

1. A system for endotracheal ventilation of a patient, said system comprising:
    an endotracheal tube and a manifold configured for allowing ventilation of the patient via said endotracheal tube;
    a first coupling means on said manifold having an axial extent, said first coupling means defining a first engagement means and comprising an exterior screw thread;
    a second coupling means on said endotracheal tube having an axial extent, said second coupling means defining a second engagement means and comprising an exterior abutment face; and
    a disengagement means mounted to said first coupling means defining an internal thread configured for cooperating with said exterior screw thread;
    wherein said system is configured to produce a locking engagement between said first and second engagement means, when said first coupling means and said second coupling means are moved together in the axial direction, and wherein said disengagement means and said exterior screw thread are configured for allowing, by rotation of the disengagement means, an axial movement of the disengagement means from a first position, wherein said first and second engagement means are in locking engagement and said disengagement means is spaced apart from said exterior abutment face, to a second position wherein said disengagement means contacts said exterior abutment face and applies an axial force on said exterior abutment face sufficient for releasing the locking engagement by forcing said first and second coupling means apart from each other, and said first coupling means together with said disengagement means are removably released from said second coupling means, said disengagement means and said second coupling means being configured so that there is no contact between said disengagement means and said second coupling means when said disengagement means is in said first position.

2. A system according to claim 1, wherein said first coupling means comprises a male coupling means; and
    said second coupling means comprises a female coupling means.

3. A system according to claim 2, wherein said male coupling means comprises a frusto-conical surface; and
    said female coupling means comprises a surface that is complementary to said frusto-conical surface.

4. A system according to claim 1, wherein said first coupling means comprises a female coupling means; and
    said second coupling means comprises a male coupling means.

5. A system according to claim 4, wherein said male coupling means comprises a frusto-conical surface; and
    said female coupling means comprises a surface that is complementary to said frusto-conical surface.

6. A system for endotracheal ventilation of a patient, comprising:
    an endotracheal tube and a manifold configured for allowing ventilation of the patient via said endotracheal tube, said endotracheal tube and said manifold each having a respective coupling means that extends along an axial direction (A) and that has respective engagement means, said engagement means being configured to releasably engage each other for establishing a releasable connection between said endotracheal tube and said manifold when said coupling means are moved together in said axial direction (A), wherein the coupling means of the manifold, in the axial direction (A), comprises an exterior screw thread, and the coupling means of the endotracheal tube comprises an exterior abutment face; and
    an annular, rotatable disengagement means with an internal thread cooperating with said exterior screw thread being rotatably mounted on said exterior screw thread of said coupling means of the manifold, and said screw thread being configured for allowing an axial movement of the disengagement means through rotation thereof from a first position, in which said engagement means engage each other to connect said endotracheal tube with said manifold and said disengagement means is spaced apart from said exterior abutment face, to a second position to separate said engagement means by said disengagement means contacting said exterior abutment face and applying a force on said exterior abutment face in said axial direction (A) sufficient to removably separate said coupling means of the manifold together said disengagement means from said coupling means of the endotracheal tube, said disengagement means and said coupling means of the endotracheal tube being configured so that there is no contact between said disengagement means and said coupling means of the endotracheal tube when said disengagement means is in said first position.

7. A system according to claim 6, wherein one coupling means is configured as a tubular male coupling means while the other coupling means is configured as a tubular female coupling means.

8. A system according to claim 7, wherein the male coupling means is configured with a frusto-conical surface forming said engagement means, and the female coupling means is configured with a surface that is complementary to said frusto-conical surface to form said engagement means of said female coupling means.

* * * * *